(12) United States Patent
Vaidya

(10) Patent No.: US 8,445,033 B2
(45) Date of Patent: May 21, 2013

(54) FORMULATION FOR PREVENTION AND TREATMENT OF BACTERIAL INFECTIONS AND PREPARATION THEREOF

(76) Inventors: Shatrughna Prasad Vaidya, Jharkhand (IN); Ram Chander Vaidya, legal representative, Hazaribag (IN)

( * ) Notice: Subject to any disclaimer, the term of this patent is extended or adjusted under 35 U.S.C. 154(b) by 0 days.

(21) Appl. No.: 13/197,131

(22) Filed: Aug. 3, 2011

(65) Prior Publication Data
US 2012/0034325 A1    Feb. 9, 2012

Related U.S. Application Data

(60) Provisional application No. 61/370,607, filed on Aug. 4, 2010.

(51) Int. Cl.
| | |
|---|---|
| A61K 36/00 | (2006.01) |
| A61K 36/8962 | (2006.01) |
| A61K 36/882 | (2006.01) |
| A61K 36/488 | (2006.01) |
| A61K 36/9068 | (2006.01) |

(52) U.S. Cl.
USPC ............................ 424/725; 424/754; 424/734

(58) Field of Classification Search
None
See application file for complete search history.

(56) References Cited

FOREIGN PATENT DOCUMENTS

| | | | |
|---|---|---|---|
| CN | 1325702 A | 12/2001 |
| CN | 1350870 A | 5/2002 |
| CN | 1569168 A | 1/2005 |
| CN | 1895580 A | 1/2007 |
| CN | 1915411 A | 2/2007 |
| CN | 101112536 A | 1/2008 |
| CN | 101199637 A | 6/2008 |
| WO | WO8804933 A1 * | 7/1988 |

OTHER PUBLICATIONS

Jeyachandran et al., Antibacterial activity of stem extracts of *Tinospora cordiolia*, Ancient Science of Life, 23(1), 40-43, 2003.
Jed Fahey, *Moriga oleifera*. A Review of the Medical Evidence for its Nutritional, Therapeutic, and Prophylactic Properties. Part 1, 2005.
Saroj K Pal, Antimicrobial Action of the Leaf Extract of *Moringa oleifera* Lam. Ancient Science of Life vol. No. XIV No. 3, Jan. 1995, pp. 197-199.
Paul Bergner et al., *Allium sativum*: Antibiotic and Immune Properties. The Healing Power of Garlic. 1995.
Aruna Bohra et al., Anti-bacterial activity of *Allium sativum* against some human and plant pathogenic bacteria. Advances in Plant Sciences, 22(2):385-386, 2009 (abstract only).

Anjana Sharma et al., Vibriocidal activity of certain medicinal plants used in Indian folklore medicine by tribals of Mahakoshal region of central India, Indian J Pharmacol. Jun. 2009; 41(3): 129-133.
Anjana Sharma et al, In Vitro Screening of the Antibacterial Activity and Identification of Bioactive compounds From Plants against Selected *Vibrio* spp. Pathogens Turk. J. Biol., vol. 33, Issue 2(May 2009), 137-144.
Monira Ahsan et al., Garlic Extract and Allicin: Broad Spectrum Antibacterial Agents Effective Against Multiple Deug Resistant Strains of *Shigella dysenteriae* type 1 and *Shigella flexneri*, Enterotoxigenic *Escheichia coli* and *Vibrio cholerae*, Phytotherapy Research; vol. 10, Issue 4, pp. 329-331, Jun. 1996 (informational page only).
Mohsen Arzanlou et al., Introducing of green garlic plant as a new source of allicin. Food Chemistry; vol. 120, issue 1, May 1, 2010, pp. 179-183 (informational page only).
Ahmad I et al., In Vitro efficacy of bioactive extracts of 15 medicinal plants against ESbeta L-producing multi drug-resistant enteric bacteria, Microbiol Res. 2007; 162(3):264-75 Epub 2006 Jul. 2007 (abstract only).
Venskutonis et al., Composition of essential Oil of Sweet Flag(*Acrous calamus* L.) leaves at different growing phases, Journal of Essential Oil research: JEOR / Sep. /Oct. 2003 (abstract only).
Asha Devi et al, Antimicrobial Activity of *Acorus calamus*(L) rhizome and Leaf extract, Acta Biologica Szegediensis, vol. 53(1): 45-49, 2009.
Timothy Motley, The Ethnobotany of Sweet Flag, *Acorus calamus* (*Araceae*) Economic Botany 48(4) pp. 397-412. 1994.
Rani P et al., Antimicrobial evaluation of some medicinal plants for their anti-enteric potential against multi-drug resistant *Salmonella typhi*. Phytother Res. Aug. 2004; 18(8):670-3 (I Can't Find a Copy of This One).
Arzanlou et al., "Inhibition of streptolysin O by allicin—an active component of garlic," Journal of Medical Microbiology 59:1044-1049, 2010.
Belguith et al., "Inhibitory effect of aqueous garlic extract (*Allium sativum*) on some isolated *Salmonella serovars*," African Journal of Microbiology Research, 4(5):328-338, Mar. 4, 2010.
Duddukuri et al., "Preliminary Studies on In Vitro Antibacterial Activity and Phytochemical Analysis of Aqueous Crude Extract of *Shorea robusta* Floral Parts," International Journal of Current Research, 3(8):021-023, Aug. 2011.

(Continued)

*Primary Examiner* — Qiuwen Mi
(74) *Attorney, Agent, or Firm* — K&L Gates LLP

(57) ABSTRACT

The invention provides a formulation for the prevention and treatment of bacterial infections by administering an effective amount of the formulation comprising an extract of at least one plant selected from *Allium sativum, Acorus calamus, Alstonia scholaris, Carissa spinarum, Cissampelos pareria, Chenopodium ambrosioides, Moringa olifera, Paederia foetida, Shorea robusta, Piper nigrum, Pueraria tuberosa, Ocimum sanctum, Terminalia bellirica, Tinospora cordifolia* and *Zingiber officinale*, and a combination thereof. The invention also provides a process for preparing and method of using the same.

7 Claims, No Drawings

OTHER PUBLICATIONS

Kalaiselvan et al., "Bark Extract of Shorea Rousta on Modulation of Immune Response in Rats," International Journal of Recent Scientific Research, 3(8):693-697, Aug. 2012.

Kumar et al., "Sensitivity of food pathogens to garlic (*Allium sativum*)," Journal of Applied Microbiology, 84:213-215, 1998.

Sousa et al., "Biological activities of extracts from *Chenopodium ambrosioides* Lineu and Kielmeyera neglecta Saddi," Annals of Clinical Microbiology and Antimicrobials 2012, 11:20.

Thankamani et al., "Phyto Chemical Screening and Anti Microbial Activity of *Alstonia scholaris* Flowers (L) R. Br. Fam: Apocyanaceae," IJPRD, 3(4):172-178, Jun. 2011.

Walter et al., "Antibacterial activity of *Moringa oleifera* and *Moringa stenopetala* methanol and n-hexane seed extracts on bacterial implicated in water borne diseases," African Journal of Microbiology Research, 5(2):153-157, Jan. 18, 2011.

Wani et al., "Wound healing activity of ethanolic extract of *Shorea robusta* Gaertn. f. resin," Indian Journal of Experimental Biology, 50:277-281, Apr. 2012.

Abdou et al., Antimicrobial Activities of *Allium sativum, Allium cepa, Raphanus sativus, Capsicum frutescens, Eruca sativa*, Allium Kurrat on Bacteria, Qual. Plant. Matter. Veg. XXII, 1:29-35, 1972.

Divya et al., "Pharmacological Activities of *Acorus calamus*: A Review," Asian Journal of Biochemical and Pharmaceutical Research, Issue 4 (vol. 1), pp. 57-64, 2011. See p. 60, "Anti-bacterial activity".

Ekwenye et al., "Antibacterial Activity of Ginger (Zingiber Officinale Roscoe and Garlic (*Allium sativum* L.) Extracts on *Escherichia coli* and *Salmonella typhi*," International Journal of Molecular Medicine and Advance Science, 1 (4):411-416, 2005.

Madani et al., "Anti-*Salmonella* activity of *Terminalia belerica*: In vitro and in vivo studies," Indian Journal of Experimental Biology, 46:817-821, Dec. 2008.

Nondo et al., "larvicidal, antimicrobial and brine shrimp activities of extracts from *Cissampelos mucronata* and *Tephrosia villosa* from coast region, Tanzania," BMC Comlementary and Alternative Medicine 2011, 11:33, 7 pgs.

Ratnam et al., "Preliminary Phytochemical and Antimicrobial Properties of *Pueraria tuberosa* (Willd.) DC: A Potential Medicinal Plant," Ethnobotanical Leaflets 13:1051-1059, 2009.

Reshmi et al., "Isolation of piperdine from *Piper nigrum* and its antiproliferative activity," Journal of Pharmacy Research 3(10):2502-2507, Oct. 2010.

Uddin et al., "In vitro antibacterial activity of the ethanol extract of *Paederia foetida* L. (*Rubiaceae*) leaves," Bangladesh J. Life Sci, 19(2):141-143, Dec. 2007.

\* cited by examiner

FORMULATION FOR PREVENTION AND TREATMENT OF BACTERIAL INFECTIONS AND PREPARATION THEREOF

REFERENCE TO RELATED APPLICATIONS

This application claims priority to and the benefit of U.S. Provisional Application No. 61/370,607, filed on Aug. 4, 2010, the entire contents of which are incorporated by reference.

FIELD OF THE INVENTION

The present invention relates to a formulation used for the prevention and treatment of bacterial infections. More particularly, it relates to an herbal formulation for the prevention and treatment of intestinal diseases such as typhoid, diarrhoea and dysentery and preparation thereof.

BACKGROUND OF THE INVENTION

Typhoid is potentially fatal infectious disease caused by bacterium *Salmonella typhi* (*S. typhi*). It is also commonly known as "Miyadi bukhar" in India.

Typhoid is a serious health problem in the developing countries; especially the parts of South East Asia and Africa, due to uncleanness and poverty.

It is evident that each year more than 600,000 deaths occur due to typhoid and similarly 16 millions suffered from the same in around the world (WHO estimation).

Common worldwide, typhoid is transmitted by the ingestion of food or water contaminated with feces from an infected person. The bacteria then perforate through the intestinal wall of healthy person and phagocytosed by macrophages. *Salmonella typhi* then alters its structure to resist destruction and allow itself to exist within the macrophage. This renders them resistant to damage by human immune system. The organism then spreads via the lymphatics while inside the macrophages. This gives them access to the reticuloendothelial system and then to the different organs throughout the body viz. liver (gall bladder), spleen, etc.

Symptoms usually develop one to three weeks after exposure, and may be mild or severe. They include high fever, malaise, headache, constipation or diarrhoea, rose-colored spots on the chest, and enlarged spleen and liver. Healthy carrier state may follow acute illness. Typhoid is also associated with various diseases such as hepatitis A, diarrhoea, dysentery, septicemia and encephalitis.

Typhoid fever can be treated with antibiotics. The following antimicrobials such as Ampicillin, chloramphenicol, trimethoprim-sulfamethoxazole, Amoxicillin and ciprofloxacin, have been commonly used to treat typhoid in developed countries.

A preventive measure to cure typhoid includes vaccination and many vaccines have been prepared using Vi antigen of *Salmonella typhi* alone or with carrier molecules.

Mainly two vaccines are currently recommended by the World Health Organization for the prevention and treatment of typhoid such as oral Ty21, a vaccine (sold as Vivotif Berna) and the injectable Typhoid polysaccharide vaccine (sold as Typhim Vi by Sanofi Pasteur and Typherix by GlaxoSmithKline). Both are between 50 to 80% protective. There exists an older Heat-killed phenol whole-cell vaccine that is still used in countries where the newer preparations are not available, but this vaccine is no longer recommended for use, because it has a higher rate of side effects mainly pain and inflammation at the site of the injection.

Several chemically synthesized or chemical based products used for the prevention and treatment of bacterial infection such as typhoid, are well known in art. However due to their chemical reactive nature, they do not find ready acceptable with living objects/organism. As opposed to a chemically reactive mixture, it may be preferable to have an environmentally safe herbal formulation derived primarily from plants and plant extracts. Hence there is a need for an herbal based formulation without any significant side effects or adverse interactions with existing medication.

Many prior-art literatures reveal the use of vaccines and antibiotics for the prevention and treatment of typhoid and other bacterial infections. For example Chinese patent CN 1,011,996,37 (A) discloses a chinese medicine decoction used for treating typhoid comprising *Atractylis ovata, Herba schizonepetae*, Hurricane lamp, Kudzuvineroot, *Pueraria lobata, Angelica*, dried orange peel, *Cassia twig, Notopterygium* root, rhizoma *Ligustici wallichii, Asarum* and *Angelica dahurica*.

Chinese patent CN1,011,125,36 (A) discloses a traditional Chinese medicine composition for treating typhoid fever and headache by internal administration. The active ingredients of the traditional Chinese medicine composition includes: 8 g of Chinese *Angelica*, 5 g of fine leaf *Shizonepeta* herb, 5 g of *Divaricate saposhnikovia* root, 5 g of incised *Notopterygium* rhizome, 5 g of *Szechuan lovage* rhizome, 3 g of manchurian wildginger, 8 g of dahurian angelica root, 5 g of tall gastrodia tuber, 4 g of Chinese ligusticum rhizome, 5 g of prepared common monkshood mother root and 4 g of liquoric root. Its advantages include low cost, high efficacy, short treatment course and durable efficacy, and the clinical verification proves that the effective rate can achieve more than 91 percent.

Chinese patent CN 1,915,411 (A) discloses Chinese medicine for treating the diseases in digestive tract, typhoid; which is prepared from liquor and twenty three Chinese-medicinal materials including cinnamon twig, white peony root, *Astragalus* root, *Coptis* root, etc.

Chinese patent CN 1,895,580 (A) discloses Chinese medicine for treating cold diseases, acyesis, menoxenia, morbid leucorrhoea, menalgia, etc and is prepared from wheat bran, broom cypress fruit, dove excrement, white cloves and black alum.

Similarly Patent No. CN 1,569,168 (A) discloses Chinese medicinal composition for treating typhoid, which is prepared from twenty eight herbs including baikal skullcap root, cork tree bark, giant knotweed rhizome, capsule of weeping forsythia, bark of peony root, radical lobelia, mulberry leaf, reed rhizome, kudzu vine root, earthworm, anemarrhena rhizome, matrimony vine, *Ligustrum japonicum, Ophiopogon* root, *Asparagus* root, Poria cocos, haw, dried orange peel, licorice root.

Another Chinese patent no. CN 1,350,870 (A) discloses Chinese medicine in the form of decoction, tablet or encapsule for treating typhoid is prepared from 25 Chinese-medicinal materials including *Ledebouriella* root, *Schizonepeta*, mint, *Notopterygium* root, *Chuan-xiong* rhizome, *dehurian angelica* root, etc. Its advantages are high effective rate up to more than 90%, and high cure rate up to more than 85%.

Chinese patent no. CN 1,325,702 (A) disclose Chinese medicine in the form of powder or pill for treating typhoid is prepared from nine Chinese-medicinal materials including *American ginseng, Stemona* root, dried ginger, *Hippophae rhamnoides*, etc. Its advantages include simple prescription and preparing process, high curative effect and short course of treatment (3-5 days).

All the available typhoid medicines and vaccines as mentioned have various side effects particularly to over aged people and Neonatal children.

Therefore to overcome these problems, there is a need of substances originating from herbal essences, in mixture or combination, with other substances constitutes, having properties of full and effective prevention of and treatment of various infectious diseases such as typhoid, while being safe for the environment and the organism (human or animal). There is a further need of a process for the preparation of such formulation.

BRIEF DESCRIPTION OF THE INVENTION

The present invention meets the aforementioned and other needs by providing formulations usable for prevention and treatment of bacterial infections. The formulation comprises an extract of at least one plant selected from *Allium sativum, Acorus calamus, Alstonia scholaris, Carissa spinarum, Cissampelos pareria, Chenopodium ambrosioides, Moringa olifera, Paederia foetida, Shorea robusta, Piper nigrum, Pueraria tuberosa, Ocimum sanctum, Terminalia bellirica, Tinospora cordifolia* and *Zingiber officinale*, and a combination thereof.

The invention also provides a process for preparing a formulation for prevention and treatment of bacterial infections. The process can include the steps of: (a) preparing an extract of at least one plant selected from *Allium sativum, Acorus calamus, Alstonia scholaris, Carissa spinarum, Cissampelos pareria, Chenopodium ambrosioides, Moringa olifera, Paederia foetida, Shorea robusta, Piper nigrum, Pueraria tuberosa, Ocimum sanctum, Terminalia bellirica, Tinospora cordifolia* and *Zingiber officinale*, and a combination thereof; (b) optionally, adding to the extract, at least one of a solvent, a stabilizer, an emulsifier, a buffer, a preservator, an enhancer, a thickener, and a combination thereof; and (c) mixing the constituents to provide the formulation.

In some embodiments, the extract is at least one of a shoot extract, a rhizome extract, a leaf extract, a seed extract, a bud extract, a tender shoot extract, a root extract, a flower extract, a fruit extract, plant bark and a combination thereof.

In some embodiments, the extract is selected from at least one of a leaf, a bud, a tender shoot, and a combination thereof.

In some embodiments, the formulation comprises at least one of a solvent, a stabilizer, an emulsifier, a buffer, a preservator, an enhancer, a thickener, and a combination thereof.

OBJECT OF THE INVENTION

Therefore, one object of the present invention is to provide a plant based herbal formulation usable for prevention and treatment of bacterial infections.

Another object of this invention is to provide a process for the preparation of the aforementioned plant based formulation usable for prevention and treatment of bacterial infections.

DETAILED DESCRIPTION OF THE INVENTION

In the following description, like reference characters designate like or corresponding parts throughout the several illustrations shown in figures/examples. It is also understood that the terms "a", "an", "the" and like are words for the sake of convenience and are not to be construct as limiting terms. Moreover, it will be understood that the illustrations are for the purpose of describing a particular exemplary embodiment of the invention and are not limit the invention thereto.

Embodiments of the present invention address the aforementioned and other needs by providing a formulation and a process for preparing the disclosed formulation.

In one embodiment, the present invention provides a formulation for prevention and treatment of bacterial infections, generally an herbal formulation. The herbal formulation of present invention comprises an extract of at least one plant selected from *Allium sativum, Acorus calamus, Alstonia scholaris, Carissa spinarum, Cissampelos pareria, Chenopodium ambrosioides, Moringa olifera, Paederia foetida, Shorea robusta, Piper nigrum, Pueraria tuberosa, Ocimum sanctum, Terminalia bellirica, Tinospora cordifolia* and *Zingiber officinale*, and a combination thereof.

In one embodiment, the present invention discloses a process for preparing the formulation. The process comprises an extract of at least one plant selected from *Allium sativum, Acorus calamus, Alstonia scholaris, Carissa spinarum, Cissampelos pareria, Chenopodium ambrosioides, Moringa olifera, Paederia foetida, Shorea robusta, Piper nigrum, Pueraria tuberosa, Ocimum sanctum, Terminalia bellirica, Tinospora cordifolia* and *Zingiber officinale*, and a combination thereof;

In one embodiment, the present invention provides a formulation comprises plant parts, preparing a solution, by optionally extracting with a solvent/water and then adding at least one of a solvent, a stabilizer, a binder, a lubricant, a thickener and a combination thereof, followed by mixing to provide the formulation of the present invention.

In one embodiment of the present invention, the extract of the tender shoot is prepared in a tablet form. In another embodiment it is prepared as a powder. The effectiveness of both forms is about the same and the choice of one over the other is only a matter of personal preferences and processing convenience. Mostly over aged people and infant prefer the powder based medicinal formulations, easy to administer.

In another embodiment, the present invention provides a formulation comprising plant extract, wherein the composition is administered atleast one of the mode of administration such as a liquid, a dry powder, a tablet, a capsule, a parenteral.

To prepare a solution based formulation, plant extracts dissolve in at least one of a solvent selected from polar, non-polar or moderately solvent. The used of solvent depend on the nature and type of active drug/molecules.

Mainly solid dosage formulation is prepare by optionally extracting with a solvent or water and then adding at least one of a solvent, a stabilizer, binder, lubricant, disintegrant, a thickener and a combination thereof, followed by mixing to provide the formulation of the present invention, wherein the extract is at least one of a shoot extract, a rhizome extract, a leaf extract, a seed extract, a bud extract, a tender shoot extract, a root extract, a flower extract, a fruit extract, and a combination thereof. Generally the extract is of tender shoot.

As stated in the preceding section of the specification, the plant extract of the present invention is typically an extract of at least one plant selected from *Allium sativum, Acorus calamus, Alstonia scholaris, Carissa spinarum, Cissampelos pareria, Chenopodium ambrosioides, Moringa olifera, Paederia foetida, Shorea robusta, Piper nigrum, Pueraria tuberosa, Ocimum sanctum, Terminalia bellirica, Tinospora cordifolia* and *Zingiber officinale*, and a combination thereof; wherein the extract is at least one of a shoot extract, a rhizome extract, a leaf extract, a seed extract, a bud extract, a tender shoot extract, a root extract, a flower extract, a fruit extract, and a combination thereof.

In one embodiment of the present invention, the extract of tender shoot is prepared in a tablet form. In another embodiment it is prepared as a powder. The effectiveness of both forms is about the same and the choice of one over the other is only a matter of preferences and processing convenience.

The same purpose may be served by optionally extracting with a solvent/water. In the solution add at least one of a solvent, a stabilizer, a thickener and a combination thereof. The solution/mixture is filtered to get final product or similar processes known to be one of the reasonable skilled in the art.

The formulation of present invention is a composition for treating intestinal infection wherein said intestinal infection is at least one of a vectorial infection, a bacterial infection, a fungal infection, a protozoan infection, a viral infection, and a combination thereof. Particularly said composition used for the treatment and prevention of bacterial infection.

Exemplary illustrations of the operation of the present invention, the practice of its formulation and the rendering of the disclosed process are described in the following examples/charts. In addition to the preferred modes of operation, a practitioner of sufficient skill in the art will appreciate that the metes and bounds of the present invention are not limited by the specific instances described herein, rather are defined by the equivalents provided by the claims of the present invention.

EXAMPLE 1

The process of preparing the formulation of the present invention generally comprises the following:

The washed and dried (at room temperature) young tender shoots of *Allium sativum, Acorus calamus, Alstonia scholaris, Carissa spinarum, Cissampelos pareria, Chenopodium ambrosioides, Moringa olifera, Paederia foetida, Shorea robusta, Piper nigrum, Pueraria tuberosa, Ocimum sanctum, Terminalia bellirica, Tinospora cordifolia* and *Zingiber officinale*, were separately grounded into fine powder. 30 gm of each powder was extracted separately at room temperature with water in about the ratio of 1:3 w/v for 24-48 hours. All the extracts thus obtained were mixed together to form a concoction and filtered using bacterial filter (0.22 mµ). From the resultant filtrate the solvent was evaporated under reduced pressure in an Eyela Centrifugal Evaporator (Japan) at 45° C. to get a semi-solid extract. Similarly a semisolid extract was obtained using methanol. Both the semisolid extracts were dried further and kept at a vacuum dessicator at 40° C. for future use. The percentage yield of both the extracts was determined and used for further experiment after suspending in suitable solution.

The aforementioned formulation appears to demonstrate very effective results ex-situ and in-situ. In the trials conducted by the inventor, by taking about 10-15 grams young tender shoots (fresh or dried) is ground along with a cup of water and filtered. The extract is given orally to the bacterial infected patient.

The said formulation used on several bacterial infected peoples and result was positive. The same formulation has been tested by Indian Council Medical Research against the causal organisms showing positive result.

In Vitro Antibacterial Activity

Initially, a total of forty fully characterised human isolates (obtained from different clinical and epidemiological studies of National Institute for Cholera and Enteric Diseases) of *Salmonella enterica* serovar Typhi, and strains of other enteric bacteria like *Vibrio cholerae* (25), *Shigella dysenteriae* (10), *Shigella flexneri* (10), *Escherichia coli* (20), along with two standard strains *E. coli* ATCC 25922 (American Type of Culture Collection, US) and *Salmonella typhi* MTCC 734 (Microbial type of Culture Collection, Chandigarh).

Media: Peptone water (PW; Oxoid brand, UK.), nutrient broth (NB; Oxoid), Mac conkey Agar (Mac; Difco, Detroit, USA), Triple sugar iron Agar (TSI, Difco, Detroit, USA) and Mueller Hinton broth (MHB; Difco, Detroit, USA) and other necessary media purchased from respective manufacturers, and peptone agar (PA), nutrient agar (NA), and Mueller Hinton agar (MHA) was prepared by adding agar to the respective liquid media, according to National Committee for Clinical Laboratory Standards guidelines (NCCLS, 2003), and used for determining minimum inhibitory concentration (MIC) of the extract.

Determination of MIC of the extracts: Both broth and agar dilution methods was used to determine the MIC of the extract with respect to different test bacteria (Chattopadhyay et al., 1998; British Society for Antimicrobial Chemotherapy. A guide to sensitivity testing, 1991). For these methods, extracts was added to each tube or plate at doubling dilutions [concentrations of 0 (control) and concentrations ranging from about 50-3000 µg/ml]. Since one solid agar medium containing the extract could be used for inoculation of a large number of bacteria at a time, this was done at least three times for every test bacterium (NCCLS protocol, 2003; Chattopadhyay et al. 1998, 2002). Further depending upon the range giving maximum activity the concentrations were narrowed down.

The preliminary In vitro antibacterial study revealed that, the both aqueous and methanolic extract of aforesaid formulation has shown considerable antibacterial activity on *S. typhi, V. cholerae* and *Shigella flexneri* and *Shigella dysenteriae* with MIC90<1000 µg/ml.

EXAMPLE 2

TABLE 1

(Minimum Inhibitory Concentration) of formulation extracts against *Salmonella typhi serovar typhi*

| Organisms | Strain number | Formulation Aqueous µg/ml. | Formulation Methanolic µg/ml. | Antibiograms (antibiotics to which the strain is resistant) |
|---|---|---|---|---|
| *Salmonella typhi serovar typhi* | A-102 | 350 | 512 | — |
| | A-118 | 350 | 450 | — |
| | A-1014 | 350 | 450 | Cr Ar SXTr Nar |
| | A-1672 | 350 | 450 | Cr Ar SXTr Nar |
| | A-2467 | 350 | 450 | — |
| | B-111 | 450 | 512 | — |
| | B-1868 | 450 | 512 | Cr Ar SXTr NAr Tr |
| | B-3235 | 350 | 512 | Cr Ar SXTr Nar |
| | B-3274 | 350 | 450 | Cr Ar SXTr Nar |
| | B-3385 | 250 | 450 | Cr Ar SXTr Nar |
| | B-7273 | 350 | 512 | — |
| | C-145 | 350 | 450 | — |
| | C-294 | 450 | 512 | — |
| | C-2114 | 350 | 450 | SXTr NAr CIPr OFXr |
| | C-2115 | 350 | 256 | SXTr NAr CIPr |
| | C-2633 | 350 | 550 | Cr Ar SXTr NAr Tr |
| | C-3482 | 350 | 450 | Cr Ar SXTr Nar |
| | C-3495 | 450 | 550 | Cr Ar SXTr Nar |
| | C-3634 | 350 | 512 | — |
| | C-3891 | 250 | 550 | — |
| | C-4401 | 350 | 450 | — |
| | C-4903 | 350 | 512 | — |
| | C-4932 | 350 | 450 | — |
| | C-5685 | 450 | 450 | — |
| | C-7087 | 350 | 512 | — |

TABLE 1-continued (Minimum Inhibitory Concentration) of formulation extracts against *Salmonella typhi serovar typhi*

| Organisms | Strain number | Formulation Aqueous µg/ml. | Formulation Methanolic µg/ml. | Antibiograms (antibiotics to which the strain is resistant) |
|---|---|---|---|---|
| | D-878 | 450 | 450 | — |
| | D-1604 | 350 | 450 | Cr Ar SXTr Nar |
| | D-1716 | 350 | 550 | Cr Ar SXTr Nar |
| | D-2190 | 350 | 450 | Cr Ar SXTr Nar |
| | D-7372 | 350 | 512 | — |
| | D-7652 | 350 | 512 | — |
| | D-7672 | 450 | 450 | — |
| | E-856 | 350 | 450 | Cr Ar SXTr Nar |
| | E-860 | 350 | 512 | Cr Ar SXTr Nar |
| | E-1349 | 350 | 512 | — |
| | E-1590 | 250 | 450 | Cr Ar SXTr Nar |
| | E-2990 | 350 | 450 | — |
| | E-3316 | 350 | 450 | — |
| | E-3404 | 350 | 450 | — |
| | G-1846 | 450 | 512 | — |
| *S. typhi* | MTCC734 | 350 | 550 | — |

Ar—ampicillin resistant; Cr—chloramphenicol resistant; Tr—tetracycline resistant; Qr—cotrimoxazole resistant; NAr—nalidixic Acid resistant; NORr—norfloxacin resistant; SXTr—sulphamethoxazole and trimethoprim resistant; CIPr—ciprofloxacin resistant; OFXr—, ofloxacin resistant; Amcr—amoxicillin with clavulanic acid resistant; CTXr—cefotaxime resistant; NORr—norfloxacin resistant.

EXAMPLE 3

TABLE 2

Minimum inhibitory concentrations (MIC) of formulation extracts against *Vibrio cholerae*

| Organisms | Strain number | Formulation Aqueous µg/ml. | Formulation Methanolic µg/ml. | Antibiograms (antibiotics to which the strain is resistant) |
|---|---|---|---|---|
| | A-5345 | 850 | 500 | — |
| | A-5351 | 850 | 500 | — |
| *V. cholerae* | A-5361 | 850 | 550 | — |
| | A-5363 | 850 | 500 | — |
| | A-5382 | 850 | 500 | — |
| | B-10079 | 850 | 500 | — |
| | C-11360 | 850 | 500 | — |
| | C-11374 | 850 | 500 | — |
| | C-11386 | 900 | 500 | — |
| | F-3004 | 850 | 500 | — |
| | F-3010 | 850 | 500 | — |
| | F-3017 | 900 | 500 | — |
| | F-3020 | 850 | 550 | — |
| | F-3025 | 850 | 500 | — |
| | F-3044 | 850 | 550 | — |
| | F-3071 | 850 | 500 | — |
| | F-3080 | 850 | 500 | — |
| | F-3093 | 850 | 550 | — |
| | F-3120 | 850 | 500 | — |
| | F-3449 | 850 | 500 | — |
| | F-3462 | 900 | 500 | — |
| | F-3463 | 850 | 500 | — |
| | G-3248 | 850 | 500 | — |
| | G-3289 | 850 | 500 | — |
| | K-1510 | 850 | 500 | — |
| *E. coli* ATCC | 25922 | 850 | 550 | — |

TABLE 3

Minimum inhibitory concentration of formulation extracts against *Shigella* Sp.

| Organisms | Strain number | Formulation Aqueous µg/ml. | Formulation Methanolic µg/ml. | Antibiograms (antibiotics to which the strain is resistant) |
|---|---|---|---|---|
| *S. flexneri* 2a | 7061 | 150 | 150 | Ar Cr Tr Qr NAr NORr CIPr OFXr Amcr |
| | 7062 | 150 | 200 | Ar Cr Tr Qr NAr NORr CIPr OFXr Amcr |
| | 7103 | 150 | 150 | Ar Cr Tr Qr NAr NORr CIPr OFXr Amcr |
| | 7146 | 150 | 200 | Ar Cr Tr Qr NAr NORr CIPr OFXr Amcr |
| | 7151 | 200 | 200 | Ar Cr Tr Qr NAr NORr CIPr OFXr Amcr |
| | 7160 | 150 | 150 | Ar Cr Tr Qr NAr NORr CIPr OFXr Amcr |
| | 7163 | 150 | 150 | Ar Cr Tr NAr NORr CIPr OFXr Amcr |
| | 7171 | 150 | 150 | Ar Cr Tr Qr NAr NORr CIPr OFXr Amcr |
| | 7179 | 150 | 150 | Ar Cr Tr NAr NORr CIPr OFXr Amcr |
| | 7217 | 200 | 150 | Ar Cr Tr Qr NAr NORr CIPr OFXr Amcr |
| | 7244 | 150 | 150 | Ar Cr Tr Qr NAr CIPr OFXr Amcr |
| *S. dysenteriae*1 | 4446 | 550 | 700 | Ar Cr Tr Qr NAr NORr CIPr Amx* |
| | 4717 | 550 | 700 | Ar Cr T* Qr NAr NORr CIPr |
| | 4834 | 600 | 800 | Ar Cr Tr Qr NAr CIPr Amxr |
| | 4906 | 550 | 700 | Ar Cr TrQr NAr NORr CIPr Amxr |
| | 4957 | 550 | 800 | Ar Cr Tr Qr NAr NORr CIPr Amx* |
| | 5168 | 550 | 700 | Ar Cr Tr Qr NAr NORr CIPr Amx* |
| | 5235 | 550 | 700 | Ar Cr Tr Qr NAr NORr CIPr Amxr |
| | 5282 | 600 | 800 | Ar Cr Tr Qr NAr NORr CIPr Amx* |
| | 5287 | 550 | 700 | Ar Cr Tr Qr NAr NORr CIPr Amxr CTX* |
| *E. coli* ATCC | 25922 | 800 | 800 | — |

Ar—ampicillin resistant; Cr—chloramphenicol resistant; Tr—tetracycline resistant; Qr—cotrimoxazole resistant; NAr—nalidixic Acid resistant; NORr—norfloxacin resistant; SXTr—sulphamethoxazole and trimethoprim resistant; CIPr—ciprofloxacin resistant; OFXr—ofloxacin resistant; Amcr—amoxicillin with clavulanic acid resistant; NAr—nalidixic acid resistant; CTXr—cefotaxime resistant; NORr—norfloxacin resistant; *—intermediate; T*—tetracycline intermediate resistant; CTX*—cefotaxime intermediate resistant; Amxr—amoxicillin resistant; Amx*—amoxicillin intermediate resistant

TABLE 4

Minimum inhibitory concentration of formulation extracts against *E. coli*.

| Organisms | Strain number | formulation Aqueous µg/ml. | formulation Methanolic µg/ml. | Antibiograms (antibiotics to which the strain is resistant) |
|---|---|---|---|---|
| *E. coli* (EAEC) | BCH-104 | 2300 | 2800 | — |
| | BCH-135 | 2200 | 2800 | — |
| | BCH-152 | 2200 | 2800 | — |
| | BCH-157 | 2200 | 2900 | — |
| | BCH-189 | 2100 | 2600 | — |

TABLE 4-continued

Minimum inhibitory concentration of formulation extracts against *E. coli*.

| Organisms | Strain number | formulation | | Antibiograms |
| | | Aqueous µg/ml. | Methanolic µg/ml. | (antibiotics to which the strain is resistant) |
|---|---|---|---|---|
| | BCH-197 | 2200 | 2900 | — |
| | BCH-220 | 2200 | 2800 | — |
| | BCH-223 | 2100 | 2600 | — |
| | BCH-231 | 2300 | 2900 | — |
| | BCH-233 | 2200 | 2800 | — |
| *E. coli* ATCC | 25922 | — | — | — |

TABLE 5

Minimum inhibitory concentration (MIC) of formulation extracts against *Salmonella typhi*, *S. flexneri* 2a, *S. dysenteriae* 1, *V. cholerae* and *E. coli*.

| | | Methanolic Extract | | Aqueous Extract | |
| Organisms | Plants Name | Extract conc. (µg/ml) | Inhibited Strain numbers | Extract conc. (µg/ml) | Inhibited Strain numbers |
|---|---|---|---|---|---|
| *Salmonella typhi* serovar Typhi | formulation | 256 | 01 | 250 | 03 |
| | | 450 | 21 | 350 | 29 |
| | | 512 | 14 | 450 | 08 |
| | | 550 | 04 | — | — |
| *S. flexneri* 2a | formulation | 150 | 08 | 150 | 09 |
| | | 200 | 03 | 200 | 02 |
| *S. dysenteriae* | formulation | 700 | 06 | 550 | 07 |
| | | 800 | 03 | 600 | 02 |
| *V. cholerae* | formulation | 500 | 21 | 850 | 22 |
| | | 550 | 04 | 900 | 03 |
| *E. coli* (EAEC) | formulation | 2600 | 02 | 2100 | 02 |
| | | 2800 | 05 | 2200 | 06 |
| | | 2900 | 03 | 2300 | 02 |

Conclusion of Tables:

Work was undertaken on 40 strains of *S. typhi* (Table-1). Out of these 40 strains, 17 were found resistant to minimum 4 modern antibiotics. To all these strains the crude extract showed inhibition at the concentration ranging from 250-450 µg/ml (aqueous extract) and 256-550 µg/ml (Methanolic extract). To antibiotic non-resistant strains also inhibition concentration was ranging from 250-550 µg/ml.

On a similar pattern the formulation extract was tested against 25 strains of *Vibrio chloreae* non-resistant strains (Table-2). Interestingly extract was inhibitory to *V. chloreae* also at 500-900 µg/ml.

Encouraging results were obtained for all antibiotic resistant strains of *Shigella* sp. Range of concentration was 150-200 µg/ml for *S. flexneri* 2a and 550-800 µg/ml for *S. dysenteriae* (Table-3).

On further test against *E. coli* (10strains), extract was effective at slightly higher concentration of 2100-2900 µg/ml.

Table 5 summarizes the entire experimentation highlighting the potential of the formulation extracts against typhoid and related disease causing bacterial, even in its crude form as compared to the purified form of modern antibiotics.

The amount of formulation used for prevention and treatment of bacterial infections is usually sufficient for usage by individual user or by a number of users. It is generally possible to additively scale up the quantities depending upon need, by proportionately scaling up of the constituents. It would be possible, without undue experimentation, to one of ordinary skill in the art to perform the scale-up of the formulations to nearly a thousand-fold capacity of the formulation, without substantive loss in formulation efficacy.

While the invention may be susceptible to various modifications and alternative forms, specific embodiments have been shown by way of example and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A process for preparing a formulation for treatment of bacterial infections, said process comprising the step of:
    (a) preparing an extract of each of the following plants: *Allium sativum, Acorus calamus, Alstonia scholaris, Carissa spinarum, Cissampelos pareira, Chenopodium ambrosioides, Moringa oleifera, Paederia foetida, Shorea robusta, Piper nigrum, Pueraria tuberosa, Ocimum sanctum, Terminalia bellirica, Tinospora cordifolia* and *Zingiber officinale*; and
    (b) mixing the extracts to provide the formulation.

2. The process of claim 1, wherein the extract is at least one of a shoot extract, a rhizome extract, a leaf extract, a seed extract, a bud extract, a tender shoot extract, a root extract, a flower extract, a fruit extract, plant bark extract and a combination thereof.

3. The process of claim 1, wherein the extract is selected from at least one of a leaf, a bud, a tender shoot, and a combination thereof.

4. The process of claim 1, wherein the formulation comprises at least one of a solvent, a stabilizer, an emulsifier, a buffer, a preservative, an enhancer, a thickener, and a combination thereof.

5. The process of claim 1, wherein the bacterial infection is *Salmonella typhi*.

6. The process of claim 1, wherein the bacterial infection is *Vibrio cholerae*.

7. The process of claim 1, wherein the bacterial infection is *Shigella flexneri*.

* * * * *